(12) United States Patent
Benesh et al.

(10) Patent No.: US 8,088,800 B2
(45) Date of Patent: Jan. 3, 2012

(54) 4-(5-AMINOMETHYL)-INDOLE-1-YLMETHYL)-BENZAMIDE DERIVATIVES AND RELATED COMPOUNDS AS OPIOID RECEPTOR ANTAGONISTS FOR THE TREATMENT OF OBESITY

(75) Inventors: Dana Rae Benesh, Westfield, IN (US); Maria-Jesus Blanco-Pillado, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 1510 days.

(21) Appl. No.: 10/598,281

(22) PCT Filed: Mar. 9, 2005

(86) PCT No.: PCT/US2005/007702
§ 371 (c)(1),
(2), (4) Date: Aug. 23, 2006

(87) PCT Pub. No.: WO2005/090303
PCT Pub. Date: Sep. 29, 2005

(65) Prior Publication Data
US 2007/0155793 A1    Jul. 5, 2007

Related U.S. Application Data

(60) Provisional application No. 60/553,176, filed on Mar. 15, 2004.

(51) Int. Cl.
*A61K 31/44* (2006.01)
*A61K 31/40* (2006.01)
*A01N 43/38* (2006.01)

(52) U.S. Cl. .................. 514/337; 514/414; 514/419

(58) Field of Classification Search .................. None
See application file for complete search history.

(56) References Cited

U.S. PATENT DOCUMENTS 4,493,843 A * 1/1985 Ashton et al. .............. 514/415
6,794,406 B2  9/2004 Haning et al.

FOREIGN PATENT DOCUMENTS

| WO | WO 02/078693 | 10/2002 |
|---|---|---|
| WO | WO 03/101963 | 12/2003 |
| WO | WO 2004/026305 | 4/2004 |
| WO | WO 2004/080968 | 9/2004 |
| WO | WO 2004/080996 | 9/2004 |
| WO | WO 2005/061442 | 7/2005 |
| WO | WO 2005/066164 | 7/2005 |
| WO | WO 2005/090286 A1 | 9/2005 |
| WO | WO 2005/090337 A1 | 9/2005 |
| WO | WO 2005/092836 A1 | 10/2005 |

OTHER PUBLICATIONS

Han (Advances in Characterization of Pharmaceutical Hydrates. Trends in Bio/Pharmaceutical Industry, pp. 25-29. Mar. 2006).*
Vippagunta et al (Adv Drug Deliv Rev 48:3-26, 2001).*
Yee, et al., "A Novel Series of Selective Leukotriene Antagonists: Exploration and Optimization of the Acidic Region in 1,6-Disubstituted Indoles and Indazoles," J. Med. Chem, vol. 33, pp. 2437-2451 (1990).
Database CA 'Online,' Chemical Abstracts Service, Rafalski, et al., "Synthesis and biological evaluation of substituted benzimidazoles—potential GPIIb/IIIa receptor antagonists," XP002332455.

* cited by examiner

*Primary Examiner* — Brandon Fetterolf
*Assistant Examiner* — Craig Ricci
(74) *Attorney, Agent, or Firm* — John C. Demeter

(57) ABSTRACT

The present invention relates to compounds of formulae (I) and (II) useful as opioid receptor antagonists for the treatment of obesity, wherein p is 0, 1, or 2; y is 0, 1, or 2; and z is 0, 1, or 2; $X_1$ is $CH_2$, CH, or N; to form a indolinyl, indolyl, or benzimidazole ring respectively and including applicable double bonds and/or hydrogen atoms; $X_2$ is CH or N; $R^1$ to $R^7$, $R^{3'}$, p, y, and z are as defined in the claims.

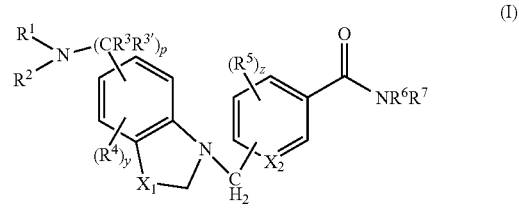

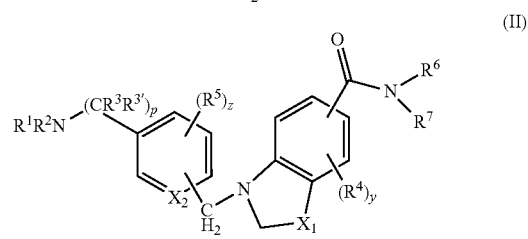

2 Claims, No Drawings

4-(5-AMINOMETHYL)-INDOLE-1-YLMETHYL)-BENZAMIDE DERIVATIVES AND RELATED COMPOUNDS AS OPIOID RECEPTOR ANTAGONISTS FOR THE TREATMENT OF OBESITY

This application is a national phase application under 35 U.S.C. Section 371 of PCT/US2005/007702, filed Mar. 9, 2005, which claims the benefit under 35 U.S.C. Section 119 (e) of U.S. provisional patent application 60/553,176, filed Mar. 15, 2004.

The present invention is in the field of medicinal chemistry. The invention relates specifically to compounds useful as opioid antagonists, methods of treatment, methods of using, and pharmaceutical compositions thereof.

BACKGROUND

Three types of opioid receptors, mu, kappa, and delta opioid receptors are generally reported. Recent evidence points to the interactions between receptor dimer combinations of mu, kappa and/or delta receptors (called heterodimers) as also contributing to opioid activity. Opioid receptors and their normal regulation or lack thereof, has been implicated in disease states including irritable bowel syndrome, nausea, vomiting, pruritic dermatoses, depression, smoking and alcohol addiction, sexual dysfunction, stroke and trauma in animals. Therefore it is not surprising that the ability to antagonistically bind opioid receptors has been shown to produce ameliorative, preventative and/or treatment effects in animals including humans afflicted with one or more of these disease states.

More recently, certain antagonists of the opioid receptors have been found to increase metabolic energy consumption, and reduction of weight in obese rats while maintaining muscle mass. These findings indicate that an effective opioid antagonist may be useful in preventing, treating and/or ameliorating the effect of obesity. Considering the percentage of the population that is obese in Western societies and the indirect costs associated with treating the effects and symptoms of obesity and Related Diseases, the importance of these findings cannot be overstated.

Though many opioid antagonists have been disclosed, the search continues for alternative and/or improved or more effective antagonists having an overall benefit to the patient with little or no major side effects. U.S. Pat. No. 4,891,379 disclosed phenylpiperidine opioid antagonists useful for the treatment of diabetes and obesity. In particular, U.S. Pat. No. 4,891,379 disclosed the compound LY 255582 represented by the structure

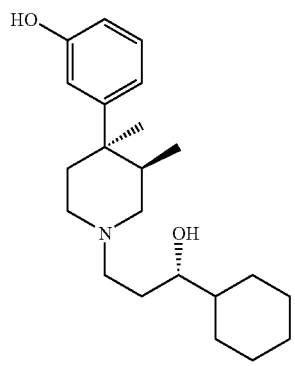

U.S. Pat. No. 4,191,771 also disclosed compounds useful as opioid antagonists. Also, bicyclic analogs of phenyl piperidine have been prepared and reported as opioid antagonists in Wentland, et al., Bioorganic and Medicinal Chemistry Letters 11 (2001) 623-626; see also Wentland, et al., Bioorganic and Medicinal Chemistry Letters 11 (2001) 1717-1721. Finally, European Patent application number EP 1 072592A2 filed May 18, 2000, discloses phenylpiperidine compounds of formula 1

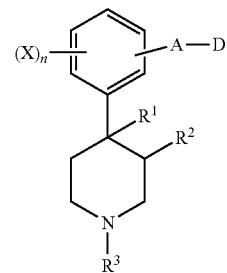

wherein A, D, $R^1$, $R^2$, $R^3$, X, and n have meanings given in the description, which are useful in the prophylaxis and in the treatment of diseases mediated by opioid receptors such as pruritus.

U.S. Pat. No. 6,140,352 discloses the compound of formula

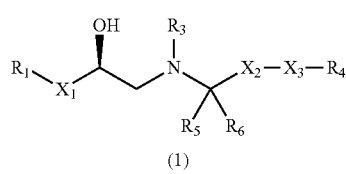

wherein the variables $X_1$, $X_2$, $X_3$ $R_1$, $R_3$, $R_4$, $R_5$ and $R_6$ are as described therein, as agonists of the beta adrenergic receptor useful for the treatment of diabetes and obesity.

Regardless of these and other disclosures of compounds useful as opioid receptor antagonists, or useful for the treatment of obesity, and/or diabetes by other mechanisms, there remains an unmet medical need for a safe, effective and/or alternate treatment or prophylaxis of diseases associated with opioid receptors, particularly obesity and Related Diseases.

SUMMARY OF THE INVENTION

The present invention provides a compound of the formula (I)

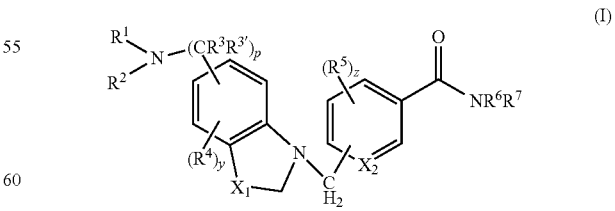

p is 0, 1, or 2;
y is 0, 1, or 2; and z is 0, 1, or 2;
$X_1$ is $CH_2$, CH, or N; to form a indolinyl, indolyl, or benzimidazole ring respectively and including applicable double bonds and/or hydrogen atoms;

$X_2$ is CH or N;

$R^1$ and $R^2$ are independently selected from hydrogen, $C_1$-$C_8$ alkyl, $C_2$-$C_8$ alkenyl, $C_2$-$C_8$ alkynyl, phenyl, $C_1$-$C_{10}$ alkylaryl, $SO_2R^8$, $(CH_2)_nC(O)NR^8R^8$, $SO_2C_1$-$C_{10}$ alkylaryl, $SO_2C_1$-$C_8$ alkylheterocyclic, $C_4$-$C_{10}$ alkylcycloalkyl, $(CH_2)_nC(O)OR^8$, and $(CH_2)_nC(O)R^8$;

wherein each of the alkyl, alkenyl, and aryl groups are optionally substituted with one to two groups independently selected from $C_1$-$C_8$ alkyl, $C_2$-$C_8$ alkenyl, phenyl, $C_3$-$C_8$ cycloalkyl, $C_1$-$C_8$ alkylaryl, and $C(O)C_1$-$C_8$ alkyl; and wherein $R^1$ and $R^2$ may optionally combine with each other to form a 4, 5, 6, or 7-membered nitrogen-containing heterocycle which nitrogen-containing heterocycle may further have substituents selected from the group consisting of oxo, amino, $C_1$-$C_8$ alkyl, $C_2$-$C_8$ alkenyl, $C_2$-$C_8$ alkynyl, phenyl, $C_1$-$C_3$ alkylaryl, $C(O)C_1$-$C_8$ alkyl, $CO(O)C_1$-$C_8$ alkyl, halo, $C_1$-$C_3$ haloalkyl;

$R^3$ and $R^{3'}$ are each independently selected from hydrogen, $C_1$-$C_8$ alkyl, $C_2$-$C_8$ alkenyl, $C_2$-$C_8$ alkynyl, phenyl, aryl, $C_1$-$C_8$ alkylcycloalkyl, and $C_1$-$C_8$ alkylaryl;

$R^4$ and $R^5$ are each independently selected from hydrogen, $C_1$-$C_8$ alkyl, $C_2$-$C_8$ alkenyl, $C_2$-$C_8$ alkynyl, $C_1$-$C_8$ alkoxy, halo, $C_1$-$C_8$ haloalkyl, phenyl, aryl, $C_1$-$C_8$ alkylaryl, $(CH_2)_mNSO_2C_1$-$C_8$ alkyl, $(CH_2)_mNSO_2$phenyl, $(CH_2)_mNSO_2$aryl, —$C(O)C_1$-$C_8$ alkyl, and —$C(O)OC_1$-$C_8$ alkyl; wherein each $R^4$ and $R^5$ is attached to its respective ring only at carbon atoms; wherein m is 1 or 2;

$R^6$ and $R^7$ are each independently selected from hydrogen, $C_1$-$C_8$ alkyl, $C_2$-$C_8$ alkenyl, $C_2$-$C_8$ alkynyl, $C(O)C_1$-$C_8$ alkyl, $SO_2C_1$-$C_8$ alkyl, $SO_2C_1$-$C_8$ alkylaryl, $SO_2C_1$-$C_8$ alkylheterocyclic, aryl, $C_1$-$C_8$ alkylaryl, $C_3$-$C_7$ cycloalkyl, $C_1$-$C_6$ alkylcycloalkyl, $(CH_2)_mC(O)OR^8$, $(CH_2)_mC(O)R^8$, $(CH_2)_mC(O)NR^8R^8$, and $(CH_2)_mNSO_2R^8$; wherein each of the alkyl, alkenyl, and aryl groups are optionally substituted with one to two groups independently selected from $C_1$-$C_8$ alkyl, $C_2$-$C_8$ alkenyl, phenyl, and $C_1$-$C_8$ alkylaryl; and wherein $R^6$ and $R^7$ may independently combine with each other, and with the nitrogen atom to which they are attached to form a 4, 5, 6, or 7-membered nitrogen containing heterocycle which nitrogen containing heterocycle may optionally have substituents selected from the group consisting of oxo, amino, $C_1$-$C_8$ alkyl, $C_2$-$C_8$ alkenyl, $C_2$-$C_8$ alkynyl, phenyl, and $C_1$-$C_8$ alkylaryl;

$R^8$ is independently selected from hydrogen, $C_1$-$C_8$ alkyl, $C_2$-$C_8$ alkenyl, phenyl, benzyl, and $C_5$-$C_8$ alkylaryl; or a pharmaceutically acceptable salt, solvate, prodrug, enantiomer, racemate, diastereomer, or mixture of diastereomers thereof.

The present invention also provides a compound of formula II

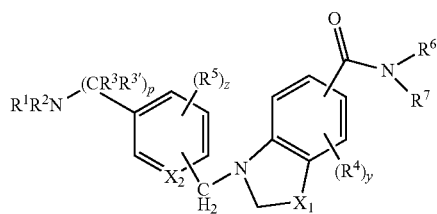

wherein p is 0, 1, or 2;

y is 0, 1, or 2; and z is 0, 1, or 2;

$X_1$ is $CH_2$, CH, or N; to form a indolinyl, indolyl, or benzimidazole ring respectively and including applicable double bonds and/or hydrogen atoms;

$X_2$ is CH or N;

$R^1$ and $R^2$ are independently selected from hydrogen, $C_1$-$C_8$ alkyl, $C_2$-$C_8$ alkenyl, $C_2$-$C_8$ alkynyl, phenyl, $C_1$-$C_{10}$ alkylaryl, $SO_2R^8$, $(CH_2)_nC(O)NR^8R^8$, $SO_2C_1$-$C_{10}$ alkylaryl, $SO_2C_1$-$C_8$ alkylheterocyclic, $C_4$-$C_{10}$ alkylcycloalkyl, $(CH_2)_nC(O)OR^8$, and $(CH_2)_nC(O)R^8$;

wherein each of the alkyl, alkenyl, and aryl groups are optionally substituted with one to two groups independently selected from $C_1$-$C_8$ alkyl, $C_2$-$C_8$ alkenyl, phenyl, $C_3$-$C_8$ cycloalkyl, $C_1$-$C_8$ alkylaryl, and $C(O)C_1$-$C_8$ alkyl; and wherein $R^1$ and $R^2$ may optionally combine with each other to form a 4, 5, 6, or 7-membered nitrogen-containing heterocycle which nitrogen-containing heterocycle may further have substituents selected from the group consisting of oxo, amino, $C_1$-$C_8$ alkyl, $C_2$-$C_8$ alkenyl, $C_2$-$C_8$ alkynyl, phenyl, $C_1$-$C_3$ alkylaryl, $C(O)C_1$-$C_8$ alkyl, $CO(O)C_1$-$C_8$ alkyl, halo, $C_1$-$C_3$ haloalkyl;

$R^3$ and $R^{3'}$ are each independently selected from hydrogen, $C_1$-$C_8$ alkyl, $C_2$-$C_8$ alkenyl, $C_2$-$C_8$ alkynyl, phenyl, aryl, $C_1$-$C_8$ alkylcycloalkyl, and $C_1$-$C_8$ alkylaryl;

$R^4$ and $R^5$ are each independently selected from hydrogen, $C_1$-$C_8$ alkyl, $C_2$-$C_8$ alkenyl, $C_2$-$C_8$ alkynyl, $C_1$-$C_8$ alkoxy, halo, $C_1$-$C_8$ haloalkyl, phenyl, aryl, $C_1$-$C_8$ alkylaryl, $(CH_2)_nNSO_2C_1$-$C_8$ alkyl, $(CH_2)_mNSO_2$phenyl, $(CH_2)_mNSO_2$aryl, —$C(O)C_1$-$C_8$ alkyl, and —$C(O)OC_1$-$C_8$ alkyl; wherein each $R^4$ and $R^5$ is attached to its respective ring only at carbon atoms; wherein m is 1 or 2; and n is 1, 2, or 3;

$R^6$ and $R^7$ are each independently selected from hydrogen, $C_1$-$C_8$ alkyl, $C_2$-$C_8$ alkenyl, $C_2$-$C_8$ alkynyl, $C(O)C_1$-$C_8$ alkyl, $SO_2C_1$-$C_8$ alkyl, $SO_2C_1$-$C_8$ alkylaryl, $SO_2C_1$-$C_8$ alkylheterocyclic, $C_1$-$C_8$ alkylaryl, $C_3$-$C_7$ cycloalkyl, $C_1$-$C_6$ alkylcycloalkyl, aryl, $(CH_2)_mC(O)OR^8$, $(CH_2)_mC(O)R^8$, $(CH_2)_mC(O)NR^8R^8$, and $(CH_2)_mNSO_2R^8$; wherein each of the alkyl, alkenyl, and aryl groups are optionally substituted with one to two groups independently selected from $C_1$-$C_8$ alkyl, $C_2$-$C_8$ alkenyl, phenyl, and $C_1$-$C_8$ alkylaryl; and wherein $R^6$ and $R^7$ may independently combine with each other, and with the nitrogen atom to which they are attached to form a 4, 5, 6, or 7-membered nitrogen containing heterocycle which nitrogen containing heterocycle may optionally have substituents selected from the group consisting of oxo, amino, $C_1$-$C_8$ alkyl, $C_2$-$C_8$ alkenyl, $C_2$-$C_8$ alkynyl, phenyl, and $C_1$-$C_8$ alkylaryl;

$R^8$ is independently selected from hydrogen, $C_1$-$C_8$ alkyl, $C_2$-$C_8$ alkenyl, phenyl, benzyl, and $C_5$-$C_8$ alkylaryl; or a pharmaceutically acceptable salt, solvate, prodrug, enantiomer, racemate, diastereomer, or mixture of diastereomers thereof.

The present invention also provides a method for the prevention, treatment and/or amelioration of the symptoms of obesity and Related Diseases comprising administering a therapeutically effective amount of a compound of formula (I) or II or a pharmaceutically acceptable salt, solvate, enantiomer, racemate, diastereomer or mixture of diastereomers thereof.

The present invention also provides a pharmaceutical formulation comprising a compound of formula I or II in association with a carrier, diluent and/or excipient.

The present invention also relates to a method for the treatment and/or prophylaxis of obesity and Related Diseases including eating disorders (bulimia, anorexia nervosa, etc.), diabetes, diabetic complications, diabetic retinopathy, sexual/reproductive disorders, depression, anxiety, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, hyperlipoproteinemia, substance abuse, drug overdose, compulsive behavior disorders (such as paw licking in dog), and addictive behaviors such as for example, gambling, and alcoholism, comprising administering a therapeutically effective amount of a compound of formula I or II or a pharmaceutically acceptable salt, solvate, enantiomer, racemate, diastereomer or mixture of diastereomers thereof.

The present invention relates to a compound of formula I or II useful for the manufacture of a medicament for the treatment, prevention and/or amelioration of symptoms associated with obesity and Related Diseases.

In another embodiment, the present invention relates to a compound of formula I or II or a pharmaceutically acceptable salt, solvate, enantiomer, racemate, diastereomer or mixture thereof, useful as an appetite suppressant.

The present invention relates to a method of achieving weight loss while maintaining lean muscle mass or minimizing the loss of lean muscle mass comprising administering a compound of formula I or II or a pharmaceutically acceptable salt, solvate, enantiomer, racemate, diastereomer or mixture thereof, to a patient in need thereof.

The present invention provides a compound of formula I or II useful singly or in combination with other agents approved for the treatment, prevention and/or amelioration of obesity and related diseases and symptoms thereof.

DETAILED DESCRIPTION OF THE INVENTION

As used herein, the term "patient" includes human and non-human animals such as companion animals (dogs and cats and the like) and livestock animals.

The preferred patient of treatment, amelioration and/or prevention of obesity and Related Diseases is a human.

The terms "treating" and "treat", as used herein, include their generally accepted meanings e.g. preventing, prohibiting, restraining, alleviating, ameliorating, slowing, stopping, or reversing the progression or severity of a pathological condition, or sequela thereof, described herein.

The terms "ameliorating" "preventing", "prevention of", "prophylaxis", "prophylactic" and "prevent" are used herein interchangeably and refer to reducing the severity of obesity and Related Diseases and the symptoms associated therewith, in a patient afflicted with same or reducing the likelihood that the recipient of a compound of formula I or II will be afflicted with or develop any of the pathological conditions or sequela thereof described herein.

As used herein, the term "effective amount" is synonymous with "effective dose" and means an amount of a compound of formula I or II that is sufficient in one or more administrations for preventing, ameliorating or treating a condition, or detrimental effects thereof, herein described, or an amount of a compound of formula I or II that is sufficient for antagonizing the opioid receptors to achieve the objectives of the invention.

The term "pharmaceutically acceptable" is used herein as an adjective and means substantially non-deleterious to the recipient patient.

The term "Active Ingredient" as used herein means a compound of formula I or II or a combination of a compounds of formula I or II or a combination of a compound of formula I or II and a co-antagonist of the opioid receptor or a combination a compound of formula I or II and other effective anti-obesity, weight loss or antidiabetic agent.

The term "formulation", as in pharmaceutical formulation, or "pharmaceutical composition" is intended to encompass a product comprising the Active Ingredient (as defined supra), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any effective composition made by admixing a compound of the present invention and a pharmaceutical carrier. The pharmaceutical formulations of the present invention also encompass a compound of the formula I or II and a pharmaceutically acceptable co-antagonist of opioid receptors useful for the treatment and/or prevention of obesity or Related Diseases.

The term "Related Diseases" as used herein refers to such symptoms, diseases or conditions caused by, exacerbated by, induced by or adjunct to the condition of being obese. Such diseases, conditions and/or symptoms include but are not limited to eating disorders (bulimia, anorexia nervosa, etc.), diabetes, diabetic complications, diabetic retinopathy, sexual/reproductive disorders, depression (particularly that induced by the awareness and loss of self esteem associated with obesity), anxiety, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, and hyperlipoproteinemia.

As used herein "other agents" approved for the treatment of obesity and/or related disease, or useful for weight loss and/or appetite suppression include but are not limited to Xenical®, Meridia®, Lipitor®, Crestor®, Pravachol®, Zetia®, cannabinoid receptor antagonists, and other opioid receptor antagonists.

The term "suitable solvent" refers to any solvent, or mixture of solvents, inert to the ongoing reaction that sufficiently solubilizes the reactants to afford a medium within which to effect the desired reaction.

The term "mutual solvent" means a solvent that is used to dissolve sufficiently, two or more components of a reaction or mixture separately prior to reaction or mixing, that is a solvent common to more than one reagents or components of a mixture.

The term "nitrogen containing heterocycle" refers to a monocycle which is a 4, 5, 6, or 7-member ring containing 1, 2 or 3 nitrogen atoms in addition to the carbon atoms completing the ring size, or a combination of 1 nitrogen atom and 1, or 2 atoms selected from oxygen, and sulfur in addition to the appropriate number of carbon atoms completing the ring size. A nitrogen containing heterocycle as used here may have 0, 1, 2 or 3 double bonds. A nitrogen containing heterocycle may be attached to or fused to an existing ring substituent thus forming a bicyclic or tricyclic ring system. Nonetheless, the direct result of the formation of a nitrogen containing heterocycle by the joining of two groups and the nitrogen atom to which they are attached is to form a monocycle.

The term "$C_1$-$C_8$ alkyl" or $C_{1-8}$ alkyl" refers to and includes all groups, structural isomers and/or homologues of alkyl groups having from 1 to 8 carbon atoms. When the term $C_1$-$C_8$ alkyl precedes or prefixes another group, the term $C_1$-$C_8$ alkyl, only limits the number of carbon atoms in the alkyl component. For example $C_1$-$C_8$ alkyaryl means an aryl group having a $C_1$-$C_8$ alkyl group substituent such that the number of carbon atoms in the group $C_1$-$C_8$ alkylaryl is effectively the number of carbon atoms in the aryl group plus the number of carbon atoms in the $C_1$-$C_8$ alkyl group. Similarly, the term "$C_1$-$C_8$ alkylcycloalkyl" refers to a cycloalkane group having a $C_1$-$C_8$ alkyl substituent, and wherein the entire group $C_1$-$C_8$ alkylcycloalkane may itself be a substituent attached at either the alkyl group or the cycloalkyl group to a substrate. The definition and usage applies equally to other homologues of $C_1$-$C_8$ such as for example, $C_1$-$C_7$, $C_1$-$C_6$ etc.

The term "cycloalkane" or "cycloalkyl" means cycloalkanes having from 3 to 8 carbon atoms i.e. from cyclopropane to cyclooctane.

The term "hal" or "halo" as used herein refers to a halogen including fluorine, chlorine, bromine or iodine.

As used herein the terms "alkenyl" refers to straight or branched carbon atoms having 1 or 2 carbon-carbon double bonds.

As used herein the terms "alkynyl" refers to straight or branched carbon atoms having 1 or 2 carbon-carbon triple bonds.

As used herein the term "alkoxy" refers to the group "O-alkyl" wherein alkyl is as defined previously.

The term "aryl" as used herein refers to compounds or groups having the Huckel 4n+2 pi electron arrangement and includes phenyl, benzyl, naphthyl, but excludes carbazoles and other fused tricyclic ring structures.

It is understood by one of skill in the art that where a substituent is absent, a hydrogen atom is indicated to achieve the required valency unless otherwise indicated. For example, if y is o, then $R^4$ is absent, and all applicable positions on the ring have hydrogen atoms to achieve the required valency for atoms in the ring.

As used herein, the term "protecting group" refers to a groups useful for masking reactive sites in a molecule to enhance the reactivity of another group or allow reaction at another desired site or sites following which the protecting group may be removed. Protecting groups are usually used to protect or mask groups including, but not limited to —OH, —NH, and —COOH. Suitable protecting groups are known to one of skill in the art and are described in Protecting groups in Organic Synthesis, $3^{rd}$ edition, Greene, T. W.; Wuts, P. G. M. Eds.; John Wiley and Sons, New York, 1999.

As used herein, the term "solvate" is a form of the compound of the invention wherein a crystal or crystals of a compound of the invention have been formed from a stoichiometric or non-stoichiometric amount of the compound of formula I or II and a solvent. Typical solvating solvents include for example, water, methanol, ethanol, acetone and dimethylformamide.

In those instances where a compound of the invention possesses acidic or basic functional groups, various salts may be formed which are more water soluble and/or more physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion-exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, hydrobromide, camsylate, carbonate, clavulanate, citrate, chloride, edetate, edisylate, estolate, esylate, fluoride, fumarate, gluceptate, gluconate, glutamate, glycolylarsanilate, hexylresorcinate, hydrochloride, hydroxynaphthoate, hydroiodide, isothionate, lactate, lactobionate, laurate, malate, maleate, mandelate, mesylate, methylbromide, methylnitrate, methylsulfate, sulfite, sulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

A compound of the invention as illustrated by formula I or II may occur as any one of its positional isomers, stereochemical isomers or regio-isomers, all of which are objects of the invention. Certain compounds of the invention may possess one or more chiral centers, and thus, may exist in optically active forms. Likewise, when the compounds contain an alkenyl or alkenylene group, there exist the possibility of cis- and trans-isomeric forms of the compounds. The R- and S-isomers and mixtures thereof, including racemic mixtures as well as mixtures of enantiomers or cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound i.e. a chiral resolving agent. This changes the racemic form into a mixture of stereoisomers and diastereomers, because they have different melting points, different boiling points, and different solubilities and can be separated by conventional means, such as crystallization.

The compounds of the present invention have shown inhibition of orexigenic effects, and are thus useful as appetite suppressants either as a single therapy or in conjunction with exercise and other effective appetite suppressing or weight loss medications.

PREFERRED EMBODIMENTS OF THE INVENTION

A compound of formula I or II preferably exists as the free base or a pharmaceutically acceptable salt. More preferred is the hydrochloride salt, the bisulfate salt, mesylate or the oxalic acid salt of the compound of formula I or II.

For the Groups $R^1$ and $R^2$

Preferred $R^1$ and $R^2$ groups are independently selected from the group consisting of hydrogen, methyl, ethyl, propyl, pentyl, and isopropyl. Also preferred are $R^1$ and $R^2$ groups independently selected from the group consisting of methyl, ethyl, propyl, isopropyl, phenyl,

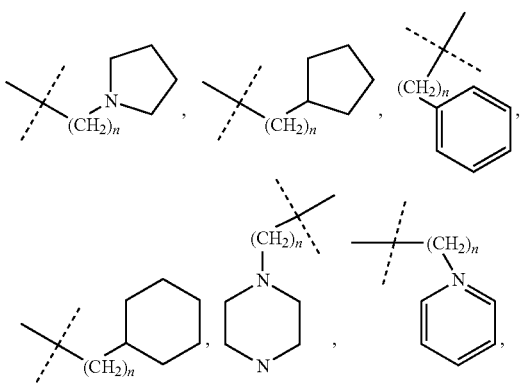

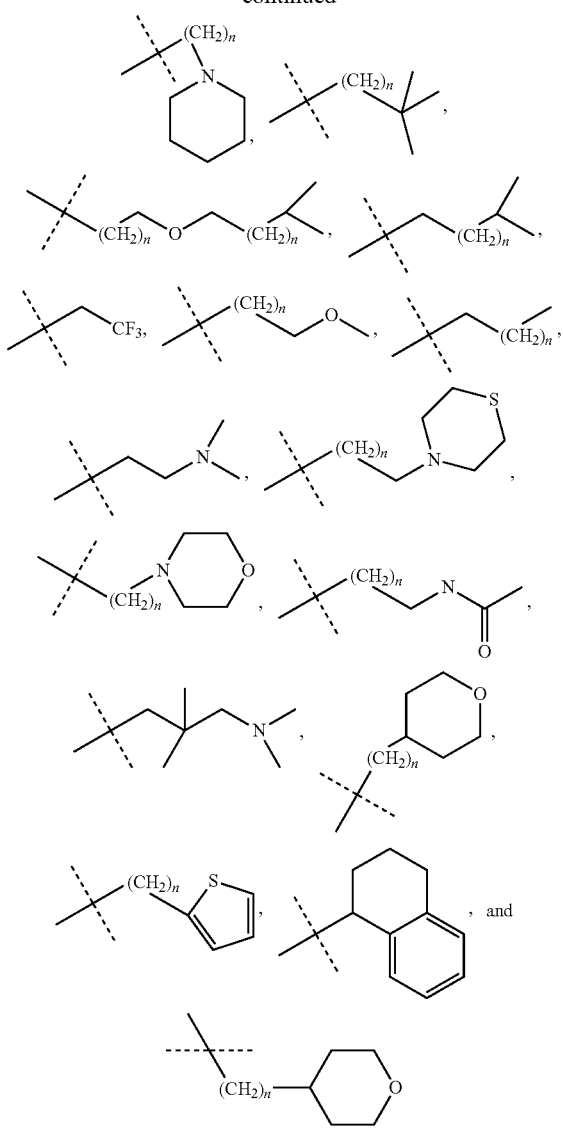

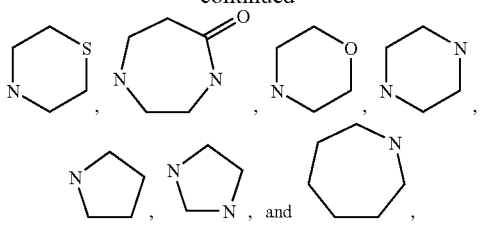

each of which is optionally substituted with a group selected from the group consisting of halogen, $C_1$-$C_8$ alkyl, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkyl heterocycle; or combine with a group selected from $C_1$-$C_8$ alkyl, halogen, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkyl heterocycle to form a substituted or unsubstituted bicycle or tricycle.

Also preferred are $R^1$ and $R^2$ groups which combine with each other to form a group selected from the group consisting of each of which is optionally substituted with a group selected from the group consisting of halogen, $C_1$-$C_8$ alkyl, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkylheterocycle.

Preferred $R^3$ and $R3'$ Groups

A preferred $R^3$ is hydrogen. A preferred $R^{3'}$ group is selected from hydrogen, methyl, ethyl, propyl, isopropyl, butyl, isobutyl, phenyl and benzyl. More preferably, both $R^3$ and $R^{3'}$ are hydrogen.

Preferred $R^4$ Groups

A preferred $R^4$ group is selected from the group consisting of hydrogen, halo, $C_1$-$C_5$ alkyl, $C_1$-$C_5$ haloalkyl, $C_1$-$C_5$ alkoxy, $C_1$-$C_5$ alkylamino, phenyl, $C_1$-$C_5$ alkylphenyl, $C_1$-$C_5$ alkylcycloalkyl, and $C_1$-$C_5$ thioalkyl. More preferred is a $R^4$ group selected from the group consisting of hydrogen, methyl, ethyl, isopropyl, chloro, fluoro, trifluoromethyl, methoxy, ethoxy, thiomethyl, phenyl, and benzyl. Most preferred is an $R^4$ group selected from the group consisting of hydrogen, methyl, ethyl, isopropyl, fluoro, chloro, trifluoromethyl, methoxy, ethoxy, propoxy, isopropoxy, and benzyl.

Though the groups $R^4$ and a $R^5$ may exist as multiple substituents on their respective ring substrates, a preferred embodiment of the invention involves compounds wherein each of $R^4$, and $R^5$ are independently absent, or singly substituted on their respective ring substrates.

Preferred $R^5$ Groups

A preferred $R^5$ group is selected from the group consisting of hydrogen, halo, $C_1$-$C_5$ alkyl, $C_1$-$C_5$ haloalkyl, $C_1$-$C_8$ alkoxy, $C_1$-$C_5$ alkylamino, phenyl, $C_1$-$C_5$ alkylphenyl, $C_1$-$C_5$ alkylcycloalkyl, and $C_1$-$C_5$ thioalkyl. More preferred is an $R^5$ group selected from the group consisting of hydrogen, methyl, ethyl, isopropyl, chloro, fluoro, trifluoromethyl, methoxy, ethoxy, thiomethyl, phenyl, and benzyl. A most preferred $R^5$ group is selected from the group consisting of hydrogen, methyl, ethyl, isopropyl, fluoro, chloro, trifluoromethyl, methoxy, ethoxy, trifluoromethoxy, and benzyl.

Preferred $R^6$ and $R^7$ Groups

Preferred are $R^6$ and $R^7$ groups independently selected from the group consisting of hydrogen, methyl, ethyl, propyl, pentyl, isopropyl, phenyl and benzyl.

Also preferred are compounds of formula I or II wherein $R^6$ and $R^7$ independently combine with each other, and with the nitrogen atom to which they are attached to form a 4, 5, 6, or 7-membered nitrogen containing heterocycle which nitrogen containing heterocycle optionally has substituents selected from the group consisting of oxo, amino, $C_1$-$C_8$ alkyl, $C_2$-$C_8$ alkenyl, $C_2$-$C_8$ alkynyl, phenyl, $C_1$-$C_8$ alkylaryl, $C(O)C_1$-$C_8$ alkyl, $CO(O)C_1$-$C_8$ alkyl, hydroxy, $C_1$-$C_8$ alkoxy, halo, and haloalkyl.

Most preferred are compounds of the invention wherein $R^6$ and $R^7$ are both hydrogen.

Preferred Values for m, and p

A preferred value for m is 1 or 2.

A preferred value for p is 0, 1, or 2. More preferred is p=1.

A preferred compound according to the present invention is a compound selected from the group consisting of:
4-{5-[(3-Methyl-butylamino)-methyl]-indol-1-ylmethyl}-benzamide,
4-{5-[(2-Thiophen-2-yl-ethylamino)-methyl]-indol-1-ylmethyl}-benzamide,
4-{5-[(3,3-Dimethyl-butylamino)-methyl]-indol-1-ylmethyl}-benzamide,
4-{5-[(2-Thiophen-2-yl-ethylamino)-methyl]-2,3-dihydro-indol-1-ylmethyl}-benzamide,
4-{5-[(3-Methyl-butylamino)-methyl]-2,3-dihydro-indol-1-ylmethyl}-benzamide,
4-{5-[(3,3-Dimethyl-butylamino)-methyl]-2,3-dihydro-indol-1-ylmethyl}-benzamide,
4-(5-Hexylaminomethyl-indol-1-ylmethyl)-benzamide,
4-{5-[(3-Phenyl-propylamino)-methyl]-indol-1-ylmethyl}-benzamide,
4-(5-{[2-(2-Fluoro-phenyl)-ethylamino]-methyl}-indol-1-ylmethyl)-benzamide,
4-{5-[(2-Hydroxy-ethylamino)-methyl]-indol-1-ylmethyl}-benzamide,
4-(5-{[2-(4-Methoxy-phenyl)-ethylamino]-methyl}-indol-1-ylmethyl)-benzamide,
4-{5-[(2-Chloro-6-fluoro-benzylamino)-methyl]-indol-1-ylmethyl}-benzamide,
4-{5-[(2-Pyridin-3-yl-ethylamino)-methyl]-indol-1-ylmethyl}-benzamide,
4-(5-{[2-(2-Ethoxy-phenyl)-ethylamino]-methyl}-indol-1-ylmethyl)-benzamide,
4-(5-{[2-(Tetrahydro-pyran-4-yl)-ethylamino]-methyl}-indol-1-ylmethyl)-benzamide,
4-{5-[(2-Cyclohex-1-enyl-ethylamino)-methyl]-indol-1-ylmethyl}-benzamide,
4-(5-{[2-(3-Fluoro-phenyl)-ethylamino]-methyl}-indol-1-ylmethyl)-benzamide,
4-{5-[(2-Ethyl-butylamino)-methyl]-indol-1-ylmethyl}-benzamide,
1-{4-[(3-Methyl-butylamino)-methyl]-benzyl}-2,3-dihydro-1H-indole-5-carboxylic acid amide or a pharmaceutically acceptable salt, solvate, enantiomer, diastereomer and diastereomeric mixture thereof.

Preparing Compounds of the Invention

Compounds of formula I or II may be prepared as described in the following schemes and/or examples or following a combination of schemes known to one of skill in the art for making fragments and combinations thereof. Compounds employed as initial starting materials in the synthesis of compounds of the invention are well known and, to the extent not commercially available, are readily synthesized using specific references provided, or by standard procedures commonly employed by those of ordinary skill in the art and/or found in general reference texts.

More particularly, the compounds of the invention are produced in accordance with schemes 1 through 3 that are described in detail below, or analogous methods thereto. These reactions are often carried out following known procedures, methods, or analogous methods thereto. Examples of such known procedures and/or methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001; Advanced Organic Chemistry, 4$^{th}$ Edition, Part B, Reactions and Synthesis, Francis A. Carey and Richard J. Sundberg, Kluwer Academic/Plenum Publishers, 2000, etc., and references cited therein.

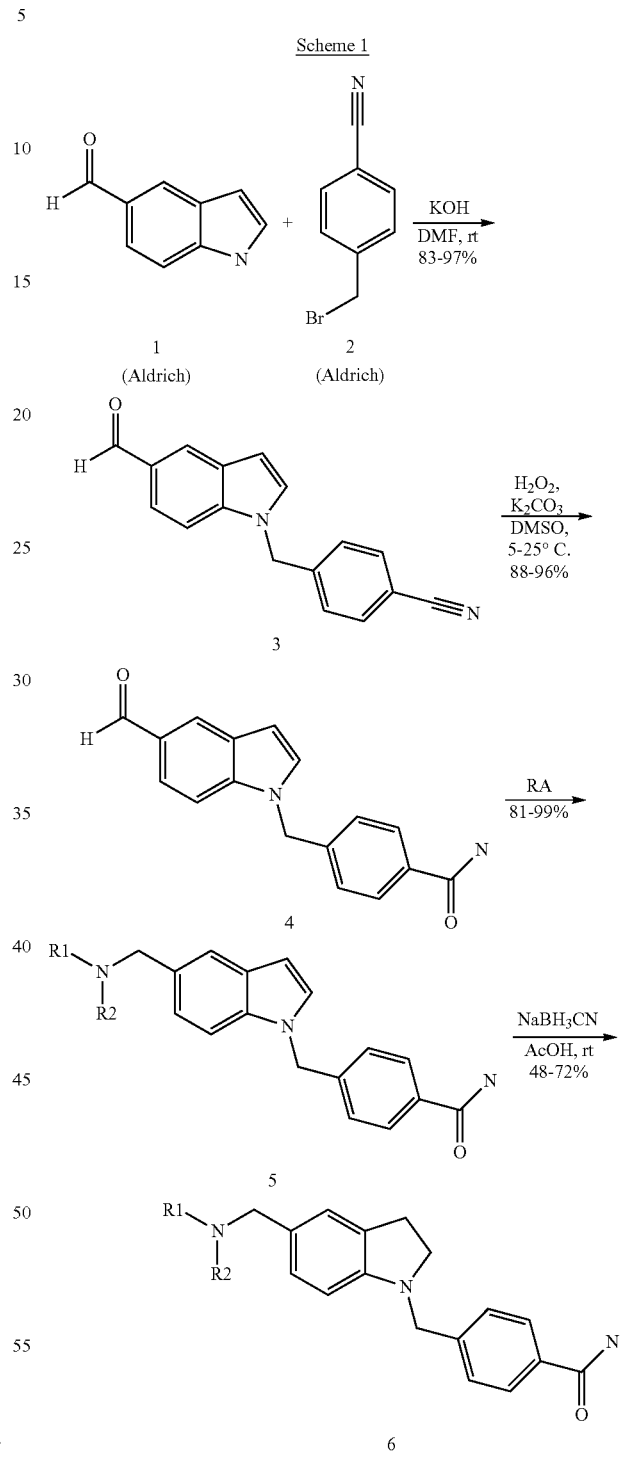

Treatment of indole 1 with benzylic bromide 2 in the presence of KOH affords the nitrile 3. Hydrolysis of the nitrile 3 with potassium carbonate and hydrogen peroxide provides the corresponding carboxamide 4. Reductive amination of the benzylic aldehyde 4 with a desired amine affords the desired analogs 5 of a compound of formula I. Further treatment of compound 5 with sodium cyanoborohydride or other suitable reducing agent affords the corresponding indoline 6, also a compound of the invention.

Benzimidazole analogs of compounds of formula I may be prepared as shown in scheme 2. Telaty, C. N. et al., (*J. Heterocyclic Chemistry*, 1976, 13, 1121) has reported the preparation of the aldehyde 7 and/or analogs thereof. Treatment of the aldehyde 7 with 4-bromomethylbenzonitrile (8) in the presence of a strong base (KOH, NaOH) in DMF (or DMA) affords the coupled nitrile 9. The nitrile 9 could be hydrolyzed with hydrogen peroxide in the presence of potassium carbonate to afford the carboxamide 10. The aldehyde functionality of the carboxamide 10 could be reacted with different basic amines to form the corresponding imine followed by reduction with sodium borohydride to form compound 11, a compound of formula I.

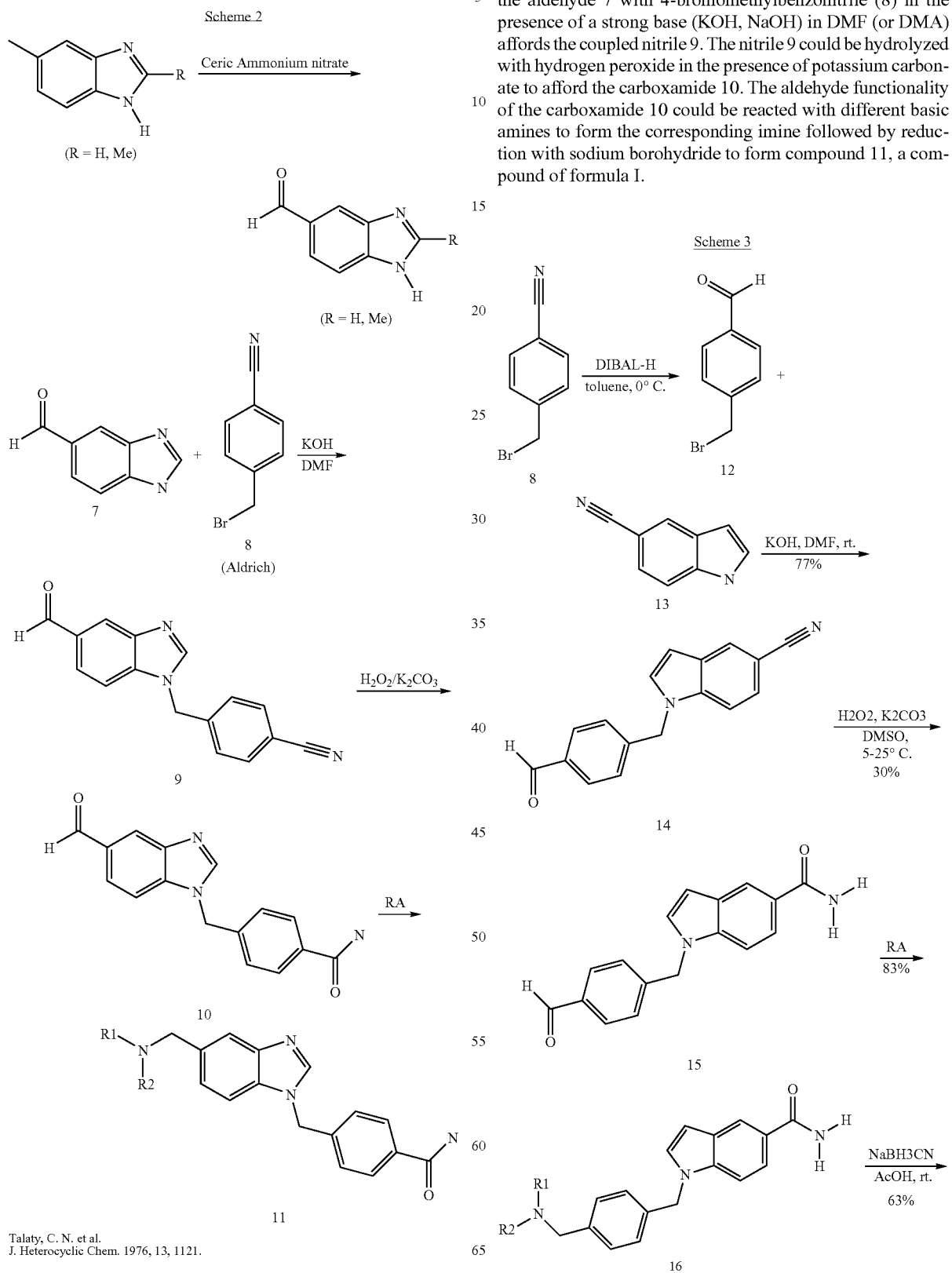

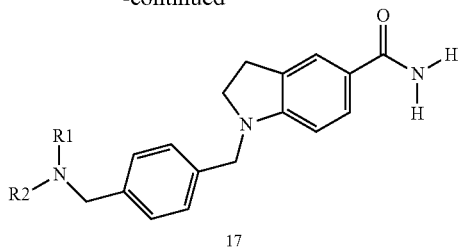

Reduction of nitrile 8 using for example diisobutylaluminum hydride (DIBAL-H) affords 4-bromomethyl benzaldehyde (12). Similarly, treatment of 12 with the cyanoindole 13 affords the coupled product 14. The nitrile group of compound 14 is hydrolyzed with potassium carbonate and hydrogen peroxide to obtain the carboxamide 15. Reductive amination of 15 with a variety of primary and secondary amines affords the desired analogs 17, a compound of formula II. Compound 17 may be treated with a reductive agent, e.g. sodium cyanoborohydride to obtain the corresponding indoline compounds of formula II.

Method of Using the Invention

As noted above, the compounds of the present invention are useful in blocking the effect of agonists at mu, kappa, and/or delta opioid receptors. As such, the present invention also provides a method for blocking a mu, kappa, delta receptor or receptor combination (heterodimer) thereof in a mammal comprising administering to said mammal a receptor blocking dose of a compound of formula I.

The term "receptor blocking dose", as used herein, means an amount of a compound of formula I or II necessary to block a mu, kappa, or delta receptor or receptor combination (heterodimer) thereof following administration to a mammal requiring blocking of a mu, kappa, or delta receptor or receptor combination (heterodimer) thereof.

The compounds of formula I or II or combinations thereof, are effective over a wide dosage range. For example, dosages per day will normally fall within the range of about 0.05 to about 250 mg/kg of body weight. In the treatment of adult humans, the range of about 0.5 to about 100 mg/kg, in single or divided doses, is preferred. However, it will be understood that the amount of the compound actually administered will be determined by a physician in light of the relevant circumstances, including the condition to be treated, the choice of compound to be administered, the age, weight, response of the individual patient, the severity of the patient's symptoms, and the chosen route of administration. Therefore, the above dosage ranges are not intended to limit the scope of the invention in any way. The compounds may be administered by a variety of routes such as the oral, transdermal, subcutaneous, intranasal, intramuscular and intravenous routes.

A variety of physiologic functions have been shown to be subject to or influenced by mu, kappa, or delta receptors or receptor combination (heterodimers) in the brain. As such, the compounds of the present invention are believed to have the ability to treat disorders associated with these receptors or combinations thereof such as eating disorders, opioid overdose, depression, smoking, alcoholism, sexual dysfunction, shock, stroke, spinal damage and head trauma. As such, the present invention also provides methods of treating the above disorders by blocking the effect of agonists at a mu, kappa, delta receptors or receptor combinations (heterodimer) thereof.

Assay Methodology

The compounds of the present invention have been found to display significant activity in an opioid receptor binding assay which measures the ability of the compounds to block the mu, kappa, delta or receptor combination (heterodimer) thereof. The functional antagonist potency (Kb) of the sample compounds was determined using the GTPγS binding assay. GTPgS-based functional assays provide an in vitro measure of the activity of opioid agonists and antagonists. Opioid reference compounds or test compound are incubated with membrane homogenate from cells expressing the cloned human mu, kappa or delta opioid receptor and radiolabeled [35S]GTPgS. If the compound activates the opioid receptor, an increase in the binding of radiolabeled GTPgS is observed. Similarly, if the compound exhibits antagonist activity, it interferes with the ability of the control agonist to stimulate GTPgS binding. These tests provide an in vitro measurement of the activity of the compound at human opioid receptors.

GTP-γ-S Binding Assay

An SPA-based GTP-γ-S assay format was developed based on previous opioid (Emmerson et al., J. Pharm Exp Ther 278,1121,1996; Horng et al., Society for Neuroscience Abstracts, 434.6, 2000) and muscarinic (DeLapp et al., JPET 289, 946, 1999) assay formats. Membranes were resuspended in 20 mM HEPES, 100 mM NaCl, 5 mM MgCl$_2$, 1 mM DTT, and 1 mM EDTA. Fifty (50) mL of GTP-γ-[35S], compound, membrane suspension (20 microgram/well), and wheat germ agglutinin coated SPA beads (1 mg/well) were added to clear bottom 96 well assay plates. GDP (200 mM) was added to the membrane solution prior to addition to the assay plates. Plates were sealed and incubated for four hours at room temperature then placed in a refrigerator overnight to allow the beads to settle. Signal stability at 4° C. was determined to be >60 hours. Plates were warmed to room temperature and counted in a Wallac Microbeta scintillation counter. For antagonist assays, specific agonists were added at the following concentrations: (MOR) DAMGO 1 micromolar, (DOR) DPDPE 30 nM, (KOR) U69593 300 nM. Kb's were determined by Cheng-Prusoff equation (see Cheng and Prusoff, Biochem. Pharmacol. 22, 3099, 1973). Results obtained for a sample of compounds of the invention in the GTP-γ-S Binding Assay are shown in table 1 below.

TABLE 1

| Example # | Kb (nM) | | | Ki (nM) | | |
| --- | --- | --- | --- | --- | --- | --- |
| | Mu | Kappa | Delta | Mu | Kappa | Delta |
| 1 | 4.2 | 59.9 | 21.7 | 18.1 | 362.1 | 169.9 |
| 2 | 2.0 | 50.1 | 15.0 | 21.3 | 411.1 | 153.7 |
| 3 | 4.4 | 50.5 | 19.2 | 15.6 | 105.6 | 98.2 |
| 4 | 2.1 | >42.0 | 19.2 | 13.4 | 226.4 | 111 |
| 5 | 3.3 | >42.0 | 24.3 | 24.5 | 386.6 | 259.2 |
| 6 | 4.0 | 21.4 | 20.3 | 20.5 | 339.8 | 192.7 |
| 7 | 5.8 | >35.0 | 27.4 | 22.1 | 345.2 | 175.8 |
| 8 | — | — | — | 59.3 | 304.2 | 633 |
| 9 | 6.2 | >35.0 | 20.7 | 20.8 | 332.2 | 143.7 |
| 10 | — | — | — | 478.2 | 3189.7 | >5000 |
| 11 | 8.4 | >42.0 | >50.0 | 318.7 | 1114.4 | 2550.7 |

Formulation

A compound of the invention is preferably presented in the form of a pharmaceutical formulation comprising a pharmaceutically acceptable carrier, diluent or excipient and a compound of the invention. Such compositions will contain from about 0.1 percent by weight to about 90.0 percent by weight of the compound of the invention (Active Ingredient). As such, the present invention also provides pharmaceutical formulations comprising a compound of the invention and a pharmaceutically acceptable carrier, diluent or excipient therefore.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material that acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), and soft and hard gelatin capsules.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

For oral administration, the Active Ingredient, a compound of this invention, may be admixed with carriers and diluents and molded into tablets or enclosed in gelatin capsules.

The compositions are preferably formulated in a unit dosage form, each dosage containing from about 1 to about 500 mg, more usually about 5 to about 300 mg, of the Active Ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In order to more fully illustrate the operation of this invention, the following formulation examples are provided. The examples are illustrative only, and are not intended to limit the scope of the invention. The formulations may employ as Active Ingredient any of the compounds of the present invention.

Formulation 1

Hard gelatin capsules are prepared using the following ingredients:

| Compound | Amount per capsule (mg) | Concentration by weight (%) |
|---|---|---|
| Active Ingredient | 250 | 55 |
| Starch dried | 200 | 43 |
| Magnesium stearate | 10 | 2 |

The above ingredients are mixed and filled into hard gelatin capsules in 460 mg quantities.

Formulation 2

Capsules each containing 20 mg of medicament are made as follows:

| Compound | Amount per capsule (mg) | Concentration by weight (%) |
|---|---|---|
| Active Ingredient | 20 | 10 |
| Starch | 89 | 44.5 |
| Microcrystalline cellulose | 89 | 44.5 |
| Magnesium stearate | 2 | 1 |

The active ingredient, cellulose, starch and magnesium stearate are blended, passed through a No. 45 mesh U.S. sieve and filled into a hard gelatin capsule.

Formulation 3

Capsules each containing 100 mg of active ingredient are made as follows:

| Compound | Amount per capsule (mg) | Concentration by weight (%) |
|---|---|---|
| Active Ingredient | 100 | 30 |
| Polyoxyethylene Sorbitan monooleate | 50 mcg | 0.02 |
| Starch powder | 250 | 69.98 |

The above ingredients are thoroughly mixed and placed in an empty gelatin capsule.

Formulation 4

Tablets each containing 10 mg of active ingredient are prepared as follows:

| Compound | Amount per capsule (mg) | Concentration by weight (%) |
|---|---|---|
| Active Ingredient | 10 | 10 |
| Starch | 45 | 45 |
| Microcrystalline cellulose | 35 | 35 |
| Polyvinylpyrrolidone (as 10% solution in water) | 4 | 4 |
| Sodium carboxymethyl starch | 4.5 | 4.5 |
| Magnesium stearate | 0.5 | 0.5 |
| talc | 1 | 1 |

The active ingredient, starch and cellulose are passed through a No. 45 mesh U.S. sieve and mixed thoroughly. The solution of polyvinylpyrrolidone is mixed with the resultant powders, which are then passed through a No. 14 mesh U.S. sieve. The granule so produced is dried at 50-60° C. and passed through a No. 18 mesh U.S. sieve. The sodium carboxymethyl starch, magnesium stearate and talc, previously passed through a No. 60 mesh U.S. sieve, are then added to the granules, which after mixing, is compressed on a tablet machine to yield a tablet weighing 100 mg.

Formulation 5

A tablet formula may be prepared using the ingredients below:

| Compound | Amount per capsule (mg) | Percent by weight (%) |
| --- | --- | --- |
| Active Ingredient | 250 | 38 |
| Cellulose microcrystalline | 400 | 60 |
| Silicon dioxide fumed | 10 | 1.5 |
| Stearic acid | 5 | 0.5 |

The components are blended and compressed to form tablets each weighing 665 mg.

Formulation 6

Suspensions each containing 5 mg of medicament per 5 ml dose are made as follows:

| Compound | Amount per 5 mL suspension (ml) |
| --- | --- |
| Active Ingredient | 5 |
| Sodium carboxymethyl cellulose | 50 |
| Syrup | 1.25 |
| Benzoic acid solution | 0.10 |
| Flavor | q.v. |
| Color | q.v. |
| Water | q.s. to 5 mL |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

Formulation 7

An aerosol solution is prepared containing the following components:

| Compound | Concentration by weight (percent) |
| --- | --- |
| Active Ingredient | 0.25 |
| Ethanol | 29.75 |
| Propellant 22 (chlorodifluoromethane) | 70.0 |

The active compound is mixed with ethanol and the mixture added to a portion of the Propellant 22, cooled to −30° C. and transferred to a filling device. The required amount is then fed to a stainless steel container and diluted further with the remaining amount of propellant. The valve units are then fitted to the container.

EXAMPLES

In the following examples abbreviations, reaction conditions and/or common reagents known to one of skill in the art or readily available to one of skill in the art are used. The examples are not intended to limit the scope of the invention Example 1

4-{5-[(3-Methyl-butylamino)-methyl]-indol-1-ylmethyl}-benzamide

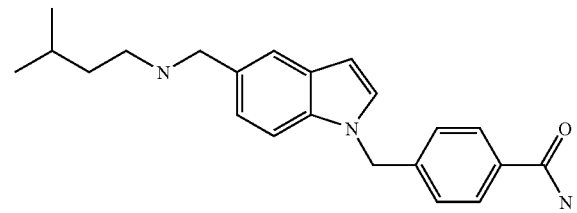

Step 1: Preparation of Intermediate 1

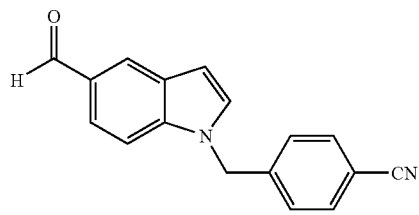

4-(5-Formyl-indol-1-ylmethyl)-benzonitrile

Mix 5-formylindole (0.50 g, 3.4 mmol), 4-bromniomethyl-benzonitrile (0.74 g, 3.8 mmol), powdered potassium hydroxide (0.23 g, 4.1 mmol) and dimethylformamide (7 mL) in a flask. Stir at rt overnight. Pour into water (20 mL) and extract with EtOAc/Hexanes (2:1, 3×50 mL). Evaporate solvents to give a yellow oil. Purification on silica using a 10% EtOAc/Hexanes to 30% EtOAc/Hexanes gradient eluent yields the product (0.75 g, 83%). Mass spectrum (ion spray): m/z=259.2 (M−1); $^1$H NMR (CDCl$_3$) 10.04 (s, 1H), 8.20 (s, 1H), 7.75 (d, J=8.6 Hz, 1H), 7.60 (d, J=8.2 Hz, 2H), 7.28 (d, J=8.5 Hz, 1H), 7.22 (d, J=3.1 Hz, 1H), 7.15 (d, J=8.2 Hz, 2H), 6.77 (d, J=3.1 Hz, 1H), 5.44 (s, 2H).

Step 2: Preparation of Intermediate 2

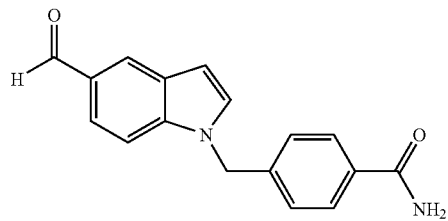

4-(5-Formyl-indol-1-ylmethyl)-benzamide

Mix 4-(5-Formyl-indol-1-ylmethyl)-benzonitrile (0.73 g, 2.8 mmol), potassium carbonate (0.19 g, 1.4 mmol), and dimethylsulfoxide (14 mL) in a flask. Cool 10 minutes in an ice bath and add hydrogen peroxide (0.95 mL, 30% wt in water) dropwise. Remove ice bath and stir at rt for 4 hrs. Pour into water (30 mL). After trituration, filter the solid formed and dry on a vacuum pump to obtain the product as a white solid (0.66 g, 88%). $^1$H NMR (DMSO-$d_6$) 9.95 (s, 1H), 8.17 (s, 1H), 7.89 (bs, 1H), 7.78 (d, J=8.1 Hz, 2H), 7.69 (d, J=3.1 Hz, 1H), 7.63-7.60 (m, 2H), 7.32 (bs, 1H), 7.23 (d, J=8.1 Hz, 2H), 6.73 (d, J=3.1 Hz, 1H), 5.54 (s, 2H).

Step 3: Preparation of Example 1

Mix 4-(5-Formyl-indol-1-ylmethyl)-benzamide (0.19 g, 0.68 mmol), isoamylamine (0.083 mL, 0.71 mmol), and methanol (5 mL) in a 20 mL vial. After the reaction mixture solubilizes, add 3 Å molecular sieves (0.50 g) and place on a rotator for 8 hrs. Remove from rotator and cool in an ice bath for 10 min. Add sodium borohydride (0.054 g, 1.43 mmol). Remove ice bath and place on a rotator for 2 hrs. Work up by placing directly onto an SCX column (5 g) using methanol to load and wash. Use 2M NH$_3$ in CH$_3$OH as eluent to obtain the product as an oil. Purification on silica using 40:1 CH$_2$Cl$_2$/2M NH$_3$ in CH$_3$OH to 20:1 CH$_2$Cl$_2$/2M NH$_3$ in CH$_3$OH gradient eluent yields the product (0.21 g, 87%). Mass spectrum (ion spray): m/z=350.2 (M+1); $^1$H NMR (DMSO-$d_6$) 7.87 (bs, 1H), 7.75 (d, J=8.1 Hz, 2H), 7.46-7.44 (m, 2H), 7.32-7.28 (m, 2H), 7.18 (d, J=8.1 Hz, 2H), 7.03 (d, J=8.6 Hz, 1H), 6.41 (d, J=3.0 Hz, 1H), 5.43 (s, 2H), 3.31 (s, 2H), 2.46 (t, J=7.7 Hz, 2H), 1.58 (septet, J=6.7 Hz, 1H), 1.31-1.25 (m, 2H), 0.81 (d, J=6.7 Hz, 6H).

Example 2

4-{5-[(2-Thiophen-2-yl-ethylamino)-methyl]-indol-1-ylmethyl}-benzamide

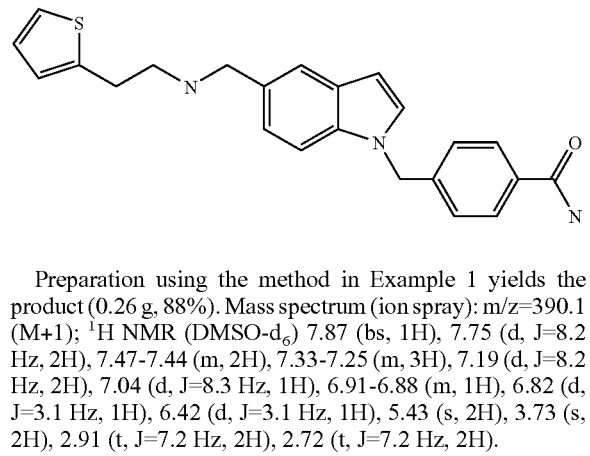

Preparation using the method in Example 1 yields the product (0.26 g, 88%). Mass spectrum (ion spray): m/z=390.1 (M+1); $^1$H NMR (DMSO-$d_6$) 7.87 (bs, 1H), 7.75 (d, J=8.2 Hz, 2H), 7.47-7.44 (m, 2H), 7.33-7.25 (m, 3H), 7.19 (d, J=8.2 Hz, 2H), 7.04 (d, J=8.3 Hz, 1H), 6.91-6.88 (m, 1H), 6.82 (d, J=3.1 Hz, 1H), 6.42 (d, J=3.1 Hz, 1H), 5.43 (s, 2H), 3.73 (s, 2H), 2.91 (t, J=7.2 Hz, 2H), 2.72 (t, J=7.2 Hz, 2H).

Example 3

4-{5-[(3,3-Dimethyl-butylamino)-methyl]-indol-1-ylmethyl}-benzamide

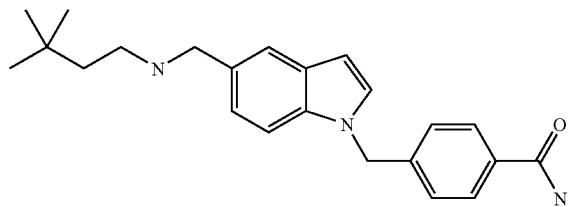

Preparation using the method of Example 1 yields the product (0.20 g, 92%). Mass spectrum (ion spray): m/z=364.2 (M+1); $^1$H NMR (DMSO-$d_6$) 7.87 (bs, 1H), 7.75 (d, J=8.1 Hz, 2H), 7.46-7.44 (m, 2H), 7.32-7.28 (m, 2H), 7.18 (d, J=8.1 Hz, 2H), 7.04 (d, J=8.3 Hz, 1H), 6.41 (d, J=3.1 Hz, 1H), 5.43 (s, 2H), 3.69 (s, 2H), 2.50-2.45 (m, 2H), 1.33 (t, J=8.1 Hz, 2H), 0.83 (s, 9H).

Example 4

4-{5-[(2-Thiophen-2-yl-ethylamino)-methyl]-2,3-dihydro-indol-1-ylmethyl}-benzamide

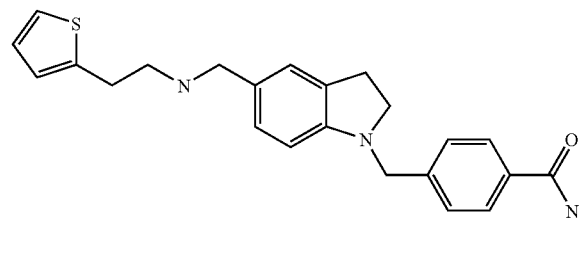

Mix 4-{5-[(2-Thiophen-2-yl-ethylamino)-methyl]-indol-1-ylmethyl}-benzamide (0.20 g, 0.51 mmol) and acetic acid (5 mL) in a flask. Add sodium cyanoborohydride (0.09 g, 1.52 mmol) and stir for 3 hrs. Neutralize reaction with 5M aqueous NaOH (10 mL) and dilute with water (50 mL). Extract with CH$_2$Cl$_2$ (3×50 mL). Purification on silica using 40:1 CH$_2$Cl$_2$/2M NH$_3$ in CH$_3$OH to 20:1 CH$_2$Cl$_2$/2M NH$_3$ in CH$_3$OH gradient eluent yields the product as an oily substance. Trituration with ether gives the product as a white solid (0.14 g, 72%). Mass spectrum (ion spray): m/z=392.2 (M+1); $^1$H NMR (DMSO-$d_6$) 7.91 (bs, 1H), 7.82 (d, J=8.1 Hz, 2H), 7.38 (d, J=7.9 Hz, 2H), 7.30 (bs, 1H), 7.27 (d, J=4.8 Hz, 1H), 6.99 (s, 1H), 6.92-6.87 (m, 2H), 6.82 (d, J=2.2 Hz, 1H), 6.46 (d, J=7.9 Hz, 1H), 4.25 (s, 2H), 3.54 (s, 2H), 3.21 (t, J=8.1 Hz, 2H), 2.92-2.81 (m, 4H), 2.69 (t, J=7.1 Hz, 2H).

Example 5

4-{5-[(3-Methyl-butylamino)-methyl]-2,3-dihydro-indol-1-ylmethyl}-benzamide

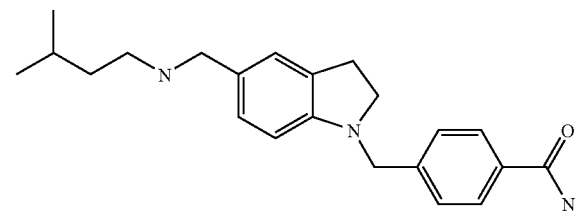

Preparation using a method similar to Example 4 yields the title product (0.078 g, 50%). Mass spectrum (ion spray) gives a fragment: m/z=265.1 [(M+1)–86]; $^1$H NMR (DMSO-$d_6$) 7.92 (bs, 1H), 7.82 (d, J=8.0 Hz, 2H), 7.39 (d, J=8.0 Hz, 2H), 7.31 (bs, 1H), 6.99 (s, 1H), 6.88 (d, J=8.0 Hz, 1H), 6.46 (d, J=7.8 Hz, 1H), 4.25 (s, 2H), 3.50 (s, 2H), 3.21 (t, J=8.3 Hz, 2H), 2.85 (t, J=8.3 Hz, 2H), 2.43 (t, J=7.2 Hz, 2H), 1.58 (septet, J=6.6 Hz, 1H), 1.30-1.24 (m, 2H), 0.82 (d, J=6.6 Hz, 6H).

Example 6

4-{5-[(3,3-Dimethyl-butylamino)-methyl]-2,3-dihydro-indol-1-ylmethyl}-benzamide

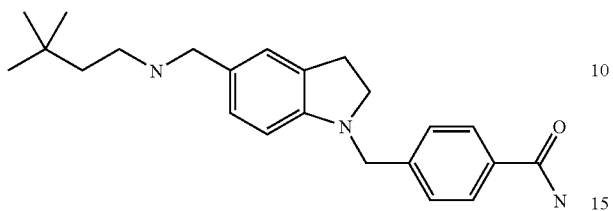

Preparation using a method similar to Example 4 yields the title product (0.076 g, 48%). Mass spectrum (ion spray) gives a fragment: m/z=265.1 [(M+1)−100]; $^1$H NMR (DMSO-$d_6$) 7.92 (bs, 1H), 7.82 (d, J=8.2 Hz, 2H), 7.39 (d, J=8.2 Hz, 2H), 7.31 (bs, 1H), 6.99 (s, 1H), 6.88 (d, J=8.2 Hz, 1H), 6.46 (d, J=7.9 Hz, 1H), 4.25 (s, 2H), 3.51 (s, 2H), 3.21 (t, J=8.2 Hz, 2H), 2.85 (t, J=8.2 Hz, 2H), 2.49-2.42 (m, 2H), 1.31 (t, J=8.1 Hz, 2H), 0.84 (s, 9H).

Example 7

4-(5-Hexylaminomethyl-indol-1-ylmethyl)-benzamide

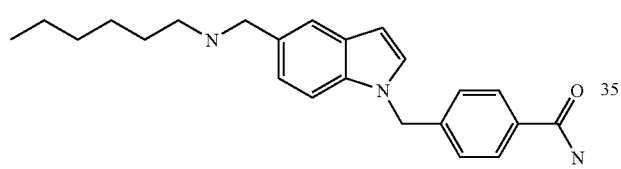

Preparation using a method similar to Example 1 yields the title product (0.27 g, 97%). Mass spectrum (ion spray): m/z=364.2 (M+1); $^1$H NMR (DMSO-$d_6$) 7.87 (bs, 1H), 7.75 (d, J=8.1 Hz, 2H), 7.46-7.43 (m, 2H), 7.31-7.28 (m, 2H), 7.18 (d, J=8.1 Hz, 2H), 7.03 (d, J=8.3 Hz, 1H), 6.41 (d, J=3.1 Hz, 1H), 5.42 (s, 2H), 3.68 (s, 2H), 2.43 (t, J=7.1 Hz, 2H), 1.41-1.33 (m, 2H), 1.28-1.16 (m, 6H), 0.81 (t, J=6.9 Hz, 3H).

Example 8

4-{5-[(3-Phenyl-propylamino)-methyl]-indol-1-ylmethyl}-benzamide

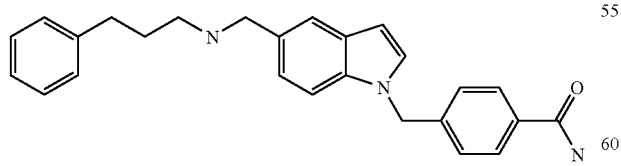

Preparation using a method similar to Example 1 yields the title product (0.26 g, 82%). Mass spectrum (ion spray): m/z=398.1 (M+1); $^1$H NMR (DMSO-$d_6$) 7.88 (bs, 1H), 7.75 (d, J=8.1 Hz, 2H), 7.46-7.43 (m, 2H), 7.32-7.28 (m, 2H), 7.22-7.08 (m, 7H), 7.04 (d, J=8.1 Hz, 1H), 6.41 (d, J=3.0 Hz, 1H), 5.42 (s, 2H), 3.69 (s, 2H), 2.56 (t, J=7.6 Hz, 2H), 1.49-1.44 (m, 2H), 1.67 (quintet, J=7.6 Hz, 2H).

Example 9

4-(5-{[2-(2-Fluoro-phenyl)-ethylamino]-methyl}-indol-1-ylmethyl)-benzamide

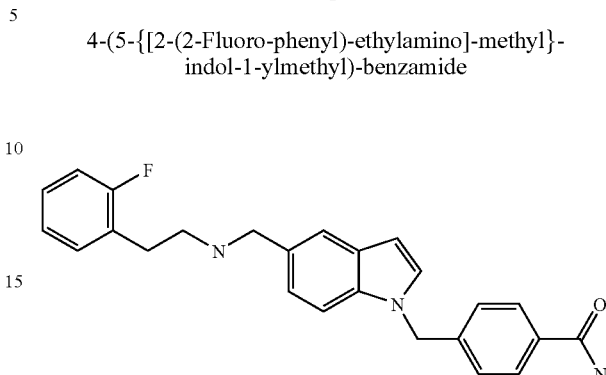

Preparation using a method similar to Example 1 yields the title product (0.28 g, 93%). Mass spectrum (ion spray): m/z=402.1 (M+1); $^1$H NMR (DMSO-$d_6$) 7.87 (bs, 1H), 7.75 (d, J=8.2 Hz, 2H), 7.45 (d, J=3.0 Hz, 1H), 7.42 (s, 1H), 7.32-7.20 (m, 4H), 7.18 (d, J=8.0 Hz, 2H), 7.11-7.04 (m, 2H), 7.02 (d, J=8.2 Hz, 1H), 6.40 (d, J=3.0 Hz, 1H), 5.42 (s, 2H), 3.72 (s, 2H), 2.75-2.56 (m, 4H).

Example 10

4-{5-[(2-Hydroxy-ethylamino)-methyl]-indol-1-ylmethyl}-benzamide

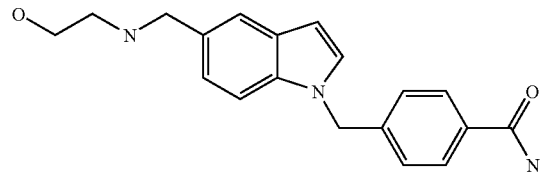

Preparation using a method similar to Example 1 yields the title product (0.25 g, 96%). Mass spectrum (ion spray): m/z=324.1 (M+1); $^1$H NMR (DMSO-$d_6$) 7.87 (bs, 1H), 7.75 (d, J=8.2 Hz, 2H), 7.46-7.44 (m, 2H), 7.32-7.28 (m, 2H), 7.18 (d, J=8.2 Hz, 2H), 7.03 (d, J=8.4 Hz, 1H), 6.41 (d, J=2.9 Hz, 1H), 5.42 (s, 2H), 4.40 (bs, 1H), 3.70 (s, 2H), 3.45-3.39 (m, 2H), 2.52 (t, J=5.7 Hz, 2H).

Example 11

4-(5-{[2-(4-Methoxy-phenyl)-ethylamino]-methyl}-indol-1-ylmethyl)-benzamide

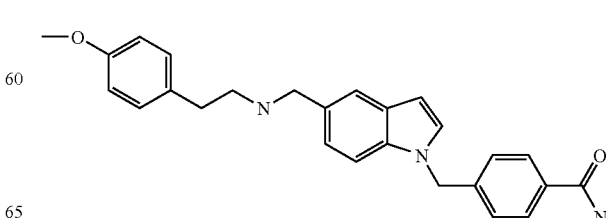

Preparation using a method similar to Example 1 yields the desired product (0.26 g, 81%). Mass spectrum (ion spray): m/z=414.1 (M+1); $^1$H NMR (DMSO-d$_6$) 7.87 (bs, 1H), 7.75 (d, J=8.0 Hz, 2H), 7.45 (d, J=3.0 Hz, 1H), 7.42 (s, 1H), 7.32-7.27 (m, 2H), 7.18 (d, J=8.0 Hz, 2H), 7.07 (d, J=8.3 Hz, 2H), 7.02 (d, J=8.6 Hz, 1H), 6.78 (d, J=8.6 Hz, 2H), 6.40 (d, J=3.0 Hz, 1H), 5.42 (s, 2H), 3.71 (s, 2H), 3.67 (s, 3H), 2.68-2.59 (m, 4H).

Example 12

4-{5-[(2-Chloro-6-fluoro-benzylamino)-methyl]-indol-1-ylmethyl}-benzamide

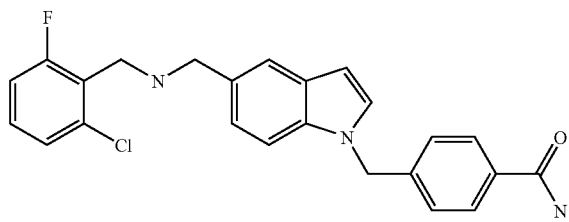

Preparation using a method similar to Example 1 yields the desired product (0.28 g, 91%). Mass spectrum (ion spray): m/z=422.1 (M+1); $^1$H NMR (DMSO-d$_6$) 7.87 (bs, 1H), 7.75 (d, J=8.2 Hz, 2H), 7.47 (s, 1H), 7.45 (d, J=2.9 Hz, 1H), 7.35-7.27 (m, 3H), 7.21-7.15 (m, 3H), 7.07 (d, J=8.3 Hz, 1H), 7.05 (d, J=8.2 Hz, 1H), 6.42 (d, J=2.9 Hz, 1H), 5.43 (s, 2H), 3.78 (s, 2H), 3.72 (s, 2H).

Example 13

4-{5-[(2-Pyridin-3-yl-ethylamino)-methyl]-indol-1-ylmethyl}-benzamide

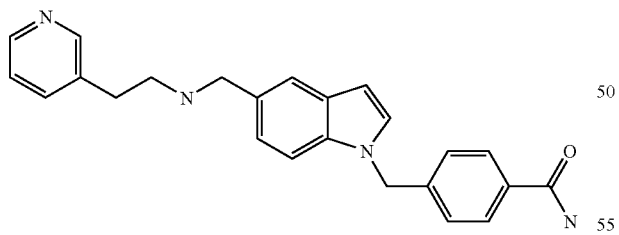

Preparation using a method similar to Example 1 yields the desired product (0.27 g, 93%). Mass spectrum (ion spray): m/z=385.2 (M+1); $^1$H NMR (DMSO-d$_6$) 8.39 (s, 1H), 8.35 (d, J=4.3 Hz, 1H), 7.87 (bs, 1H), 7.75 (d, J=7.9 Hz, 2H), 7.58 (d, J=7.9 Hz, 1H), 7.44 (d, J=2.7 Hz, 1H), 7.42 (s, 1H), 7.32-7.27 (m, 2H), 7.24 (dd, J=4.9 Hz, 7.6 Hz, 1H), 7.18 (d, J=7.9 Hz, 2H), 7.01 (d, J=8.2 Hz, 1H), 6.40 (d, J=2.7 Hz, 1H), 5.42 (s, 2H), 3.71 (s, 2H), 2.73-2.67 (m, 4H).

Example 14

4-(5-{[2-(2-Ethoxy-phenyl)-ethylamino]-methyl}-indol-1-ylmethyl)-benzamide

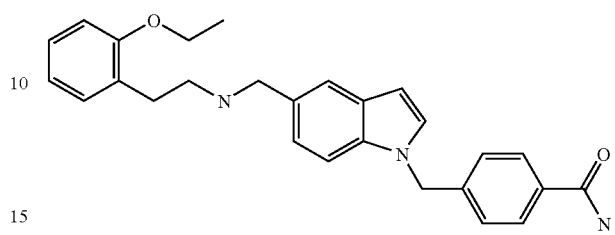

Preparation using a method similar to Example 1 yields the desired product (0.31 g, 99%). Mass spectrum (ion spray): m/z=428.2 (M+1); $^1$H NMR (DMSO-d$_6$) 7.88 (bs, 1H), 7.75 (d, J=8.2 Hz, 2H), 7.44 (d, J=3.0 Hz, 1H), 7.43 (s, 1H), 7.32-7.27 (m, 2H), 7.18 (d, J=8.2 Hz, 2H), 7.12-7.06 (m, 2H), 7.02 (d, J=8.4 Hz, 1H), 6.85 (d, J=8.2 Hz, 1H), 6.78 (t, J=7.4 Hz, 1H), 6.40 (d, J=3.0 Hz, 1H), 5.42 (s, 2H), 3.92 (q, J=6.8 Hz, 2H), 3.72 (s, 2H), 2.71-2.63 (m, 4H), 1.21 (t, J=6.8 Hz, 3H).

Example 15

4-(5-{[2-(Tetrahydro-pyran-4-yl)-ethylamino]-methyl}-indol-1-ylmethyl)-benzamide

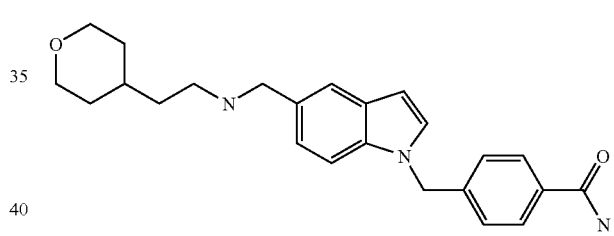

Preparation using a method similar to Example 1 yields the title product (0.28 g, 99%). Mass spectrum (ion spray): m/z=392.2 (M+1); $^1$H NMR (DMSO-d$_6$) 7.87 (bs, 1H), 7.75 (d, J=8.3 Hz, 2H), 7.46-7.43 (m, 2H), 7.31-7.28 (m, 2H), 7.18 (d, J=8.3 Hz, 2H), 7.03 (d, J=8.3 Hz, 1H), 6.41 (d, J=3.1 Hz, 1H), 5.42 (s, 2H), 3.75 (dd, J=4.2 Hz, 11.2 Hz, 2H), 3.68 (s, 2H), 3.20 (t, J=11.5 Hz, 2H), 2.49-2.44 (m, 2H), 1.55-1.43 (m, 3H), 1.35-1.27 (m, 2H), 1.12-1.01 (m, 2H).

Example 16

4-{5-[(2-Cyclohex-1-enyl-ethylamino)-methyl]-indol-1-ylmethyl}-benzamide

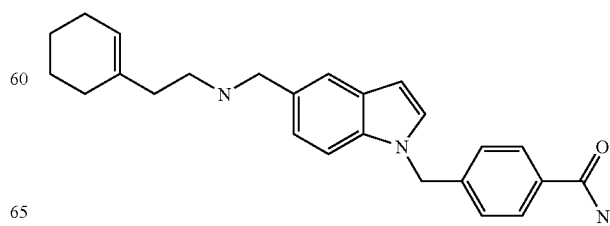

Preparation using a method similar to Example 1 yields the title product (0.26 g, 97%). Mass spectrum (ion spray): m/z=388.2 (M+1); $^1$H NMR (DMSO-d$_6$) 7.87 (bs, 1H), 7.75 (d, J=8.2 Hz, 2H), 7.45 (d, J=3.0 Hz, 1H), 7.43 (s, 1H), 7.32-7.27 (m, 2H), 7.18 (d, J=8.2 Hz, 2H), 7.02 (d, J=8.4 Hz, 1H), 6.41 (d, J=3.0 Hz, 1H), 5.42 (s, 2H), 5.33 (bs, 1H), 3.69 (s, 2H), 2.51 (t, J=7.5 Hz, 2H), 2.02 (t, J=7.1 Hz, 2H), 1.91-1.77 (m, 4H), 1.53-1.40 (m, 4H).

Example 17

4-(5-{[2-(3-Fluoro-phenyl)-ethylamino]-methyl}-indol-1-ylmethyl)-benzamide

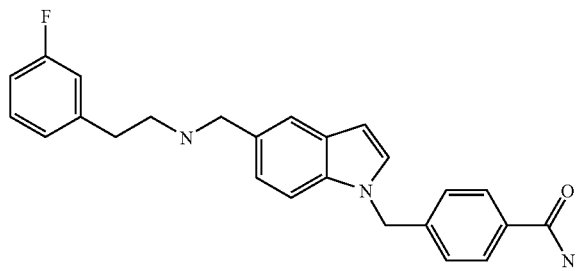

Preparation using a method similar to Example 1 yields the title product (0.27 g, 97%), Mass spectrum (ion spray): m/z=402.1 (M+1); $^1$H NMR (DMSO-d$_6$) 7.87 (bs, 1H), 7.75 (d, J=8.0 Hz, 2H), 7.45 (d, J=3.0 Hz, 1H), 7.43 (s, 1H), 7.32-7.22 (m, 3H), 7.18 (d, J=8.0 Hz, 2H), 7.04-6.92 (m, 4H), 6.40 (d, J=3.0 Hz, 1H), 5.42 (s, 2H), 3.72 (s, 2H), 2.73-2.67 (m, 4H).

Example 18

4-{5-[(2-Ethyl-butylamino)-methyl]-indol-1-ylmethyl}-benzamide

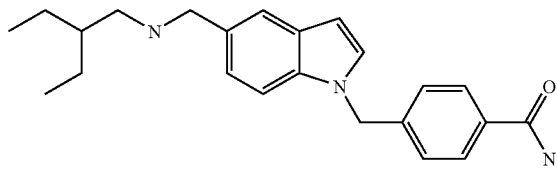

Preparation using a method similar to Example 1 yields the title product (0.26 g, 98%). Mass spectrum (ion spray): m/z=364.2 (M+1); $^1$H NMR (DMSO-d$_6$) 7.87 (bs, 1H), 7.75 (d, J=8.1 Hz, 2H), 7.44 (d, J=2.2 Hz, 2H), 7.32-7.28 (m, 2H), 7.18 (d, J=8.1 Hz, 2H), 7.04 (d, J=8.4 Hz, 1H), 6.41 (d, J=3.1 Hz, 1H), 5.42 (s, 2H), 3.68 (s, 2H), 2.35 (d, J=3.4 Hz, 2H), 1.34-1.16 (m, 5H), 0.76 (t, J=7.6 Hz, 6H).

Example 19

1-{4-[(3-Methyl-butylamino)-methyl]-benzyl}-1H-indole-5-carboxylic acid amide

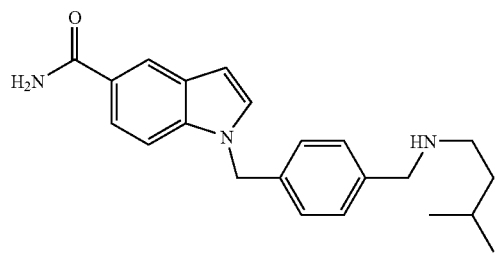

Step 1: Preparation of Intermediate 3

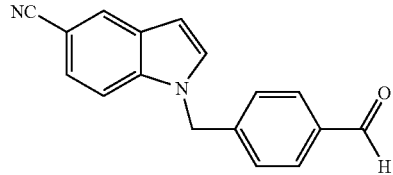

1-(4-Formyl-benzyl)-1H-indole-5-carbonitrile

Preparation using a method similar to Intermediate 1 yields the desired product (0.70 g, 77%). Mass spectrum (ion spray): m/z=259.2 (M−1); $^1$H NMR (CDCl$_3$) 9.95 (s, 1H), 7.97 (s, 1H), 7.80 (d, J=8.1 Hz, 2H), 7.36 (dd, J=1.7, 8.4 Hz, 1H), 7.28 (d, J=2.9 Hz, 1H), 7.26 (d, J=8.4 Hz, 1H), 7.20 (d, J=8.1 Hz, 2H), 6.67 (d, J=2.9 Hz, 1H), 5.44 (s, 2H).

Step 2: Preparation of Intermediate 4

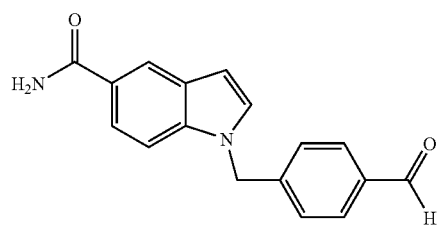

1-(4-Formyl-benzyl)-1H-indole-5-carboxylic acid amide

Preparation using a method similar to Intermediate 2 yields the desired product (0.22 g, 30%). $^1$H NMR (DMSO-d$_6$) 9.93 (s, 1H), 8.15 (s, 1H), 7.85-7.80 (m, 3H), 7.63 (d, J=8.6 Hz, 1H), 7.59 (d, J=3.2 Hz, 1H), 7.10 (bs, 1H), 6.43 (d, J=8.6 Hz, 1H), 7.33 (d, J=8.1 Hz, 2H), 6.60 (d, J=3.2 Hz, 1H), 5.57 (s, 2H).

Step 3:

Preparation using a method similar to Example 1 yields the desired product (0.21 g, 83%). $^1$H NMR (DMSO-d$_6$) 8.13 (s, 1H), 7.81 (bs, 1H), 7.63 (d, J=8.6 Hz, 1H), 7.54 (d, J=3.0 Hz, 1H), 7.46 (d, J=8.4 Hz, 1H), 7.22 (d, J=7.9 Hz, 2H), 7.12 (d, J=7.9 Hz, 2H), 7.08 (bs, 1H), 6.54 (d, J=3.0 Hz, 1H), 5.39 (s, 2H), 3.58 (s, 2H), 2.40 (t, J=6.1 Hz, 2H), 1.56 (septet, J=6.6 Hz, 1H), 1.29-1.21 (m, 2H), 0.79 (d, J=6.6 Hz, 6H).

Example 20

1-{4-[(3-Methyl-butylamino)-methyl]-benzyl}-2,3-dihydro-1H-indole-5-carboxylic acid amide

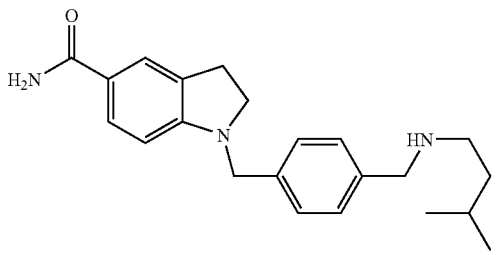

Preparation using a method similar to Example 4 yields the desired product (0.99 g, 63%). $^1$H NMR (DMSO-d$_6$) 7.58-7.51 (m, 3H), 7.26 (d, J=8.2 Hz, 2H), 7.21 (d, J=8.2 Hz, 2H), 6.84 (bs, 1H), 6.53 (d, J=8.2 Hz, 1H), 4.31 (s, 2H), 3.62 (s, 2H), 3.35 (t, J=8.4 Hz, 2H), 2.90 (t, J=8.4 Hz, 2H), 2.43 (t, J=7.5 Hz, 2H), 1.58 (septet, J=6.5 Hz, 1H), 1.31-1.24 (m, 2H), 0.91 (d, J=6.5 Hz, 6H).

We claim:

1. A compound selected from the group consisting of:
   4-{5-[(3-Methyl-butylamino)-methyl]-indol-1-ylmethyl}-benzamide,
   4-{5-[(2-Thiophen-2-yl-ethylamino)-methyl]-indol-1-ylmethyl}-benzamide,
   4-{5-[(3,3-Dimethyl-butylamino)-methyl]-indol-1-ylmethyl}-benzamide,
   4-{5-[(2-Thiophen-2-yl-ethylamino)-methyl]-2,3-dihydro-indol-1-ylmethyl}-benzamide,
   4-{5-[(3-Methyl-butylamino)-methyl]-2,3-dihydro-indol-1-ylmethyl}-benzamide,
   4-{5-[(3,3-Dimethyl-butylamino)-methyl]-2,3-dihydro-indol-1-ylmethyl}-benzamide,
   4-(5-Hexylaminomethyl-indol-1-ylmethyl)-benzamide,
   4-{5-[(3-Phenyl-propylamino)-methyl]-indol-1-ylmethyl}-benzamide,
   4-(5-{[2-(2-Fluoro-phenyl)-ethylamino]-methyl}-indol-1-ylmethyl)-benzamide,
   4-{5-[(2-Hydroxy-ethylamino)-methyl]-indol-1-ylmethyl}-benzamide,
   4-(5-{[2-(4-Methoxy-phenyl)-ethylamino]-methyl}-indol-1-ylmethyl)-benzamide,
   4-{5-[(2-Chloro-6-fluoro-benzylamino)-methyl]-indol-1-ylmethyl}-benzamide,
   4-{5-[(2-Pyridin-3-yl-ethylamino)-methyl]-indol-1-ylmethyl}-benzamide,
   4-(5-{[2-(2-Ethoxy-phenyl)-ethylamino]-methyl}-indol-1-ylmethyl)-benzamide,
   4-(5-{[2-(Tetrahydro-pyran-4-yl)-ethylamino]-methyl}-indol-1-ylmethyl)-benzamide,
   4-{5-[(2-Cyclohex-1-enyl-ethylamino)-methyl]-indol-1-ylmethyl}-benzamide,
   4-(5-{[2-(3-Fluoro-phenyl)-ethylamino]-methyl}-indol-1-ylmethyl)-benzamide,
   4-{5-[(2-Ethyl-butylamino)-methyl]-indol-1-ylmethyl}-benzamide,
   1-{4-[(3-Methyl-butylamino)-methyl]-benzyl}-2,3-dihydro-1H-indole-5-carboxylic acid amide,
   1-{4-[(3-Methyl-butylamino)-methyl]-benzyl}-1H-indole-5-carboxylic acid amide,
   or a pharmaceutically acceptable salt thereof.

2. A pharmaceutical composition comprising a therapeutically effective amount of a compound of claim 1 in association with a carrier, diluent and/or excipient.

* * * * *

UNITED STATES PATENT AND TRADEMARK OFFICE
CERTIFICATE OF CORRECTION

PATENT NO. : 8,088,800 B2  
APPLICATION NO. : 10/598281  
DATED : January 3, 2012  
INVENTOR(S) : Benesh et al.

Page 1 of 1

It is certified that error appears in the above-identified patent and that said Letters Patent is hereby corrected as shown below:

Title page, item (54) at Column 1 (Title), Line 1, delete "AMINOMETHYL)" and insert -- (AMINOMETHYL) --, therefor Title page, item (75) at Column 1 (Inventors), Line 1, delete "Raε" and insert -- Rae --, therefor.

At Column 1, Line 1, delete "AMINOMETHYL)" and insert -- (AMINOMETHYL) --, therefor.

Signed and Sealed this
Twenty-eighth Day of February, 2012

David J. Kappos
*Director of the United States Patent and Trademark Office*